(12) United States Patent
Watanabe et al.

(10) Patent No.: US 7,561,663 B2
(45) Date of Patent: Jul. 14, 2009

(54) X-RAY DETECTION DEVICE FOR FOREIGN MATTER

(75) Inventors: Toshihisa Watanabe, Atsugi (JP);
Hiroaki Kobayashi, Atsugi (JP)

(73) Assignee: Anritsu Industrial Solutions Co., Ltd., Atsugi-shi, Kanagawa-ken (JP)

( * ) Notice: Subject to any disclaimer, the term of this patent is extended or adjusted under 35 U.S.C. 154(b) by 646 days.

(21) Appl. No.: 10/582,665

(22) PCT Filed: Jun. 22, 2005

(86) PCT No.: PCT/JP2005/011875
§ 371 (c)(1),
(2), (4) Date: Jun. 13, 2006

(87) PCT Pub. No.: WO2006/001465
PCT Pub. Date: Jan. 5, 2006

(65) Prior Publication Data
US 2009/0154643 A1 Jun. 18, 2009

(30) Foreign Application Priority Data
Jun. 24, 2004 (JP) .............................. 2004-186682

(51) Int. Cl.
*G01F 1/66* (2006.01)
(52) U.S. Cl. ........................................ 378/51; 378/207

(58) Field of Classification Search ............. 378/51–58, 378/207
See application file for complete search history.

(56) References Cited

U.S. PATENT DOCUMENTS 4,791,655 A * 12/1988 Nagata et al. .................. 378/57
6,449,334 B1 * 9/2002 Mazess et al. ................ 378/53

FOREIGN PATENT DOCUMENTS

| JP | 03-057946    | 3/1991  |
|----|--------------|---------|
| JP | 2002-131244  | 5/2002  |
| JP | 2003-315286  | 11/2003 |
| JP | 2004-125715  | 4/2004  |

* cited by examiner

*Primary Examiner*—Hoon Song
(74) *Attorney, Agent, or Firm*—Manabu Kanesaka

(57) ABSTRACT

An X-ray detection device for detecting whether or not foreign matter is mixed in on the basis of the transmission amount of X-rays that have penetrated an examination subject article by applying X-rays, at a predetermined detection position to an examination subject article being conveyed in a pipe (7), wherein a test-piece table (17) capable of passing by the detection position at substantially the same speed as that of the examination subject article is installed in the vicinity of the pipe (7), with a test-piece (21) placed thereon. X-ray detection sensitivity can be detected without mixing the test-piece in the actual examination subject article.

7 Claims, 8 Drawing Sheets

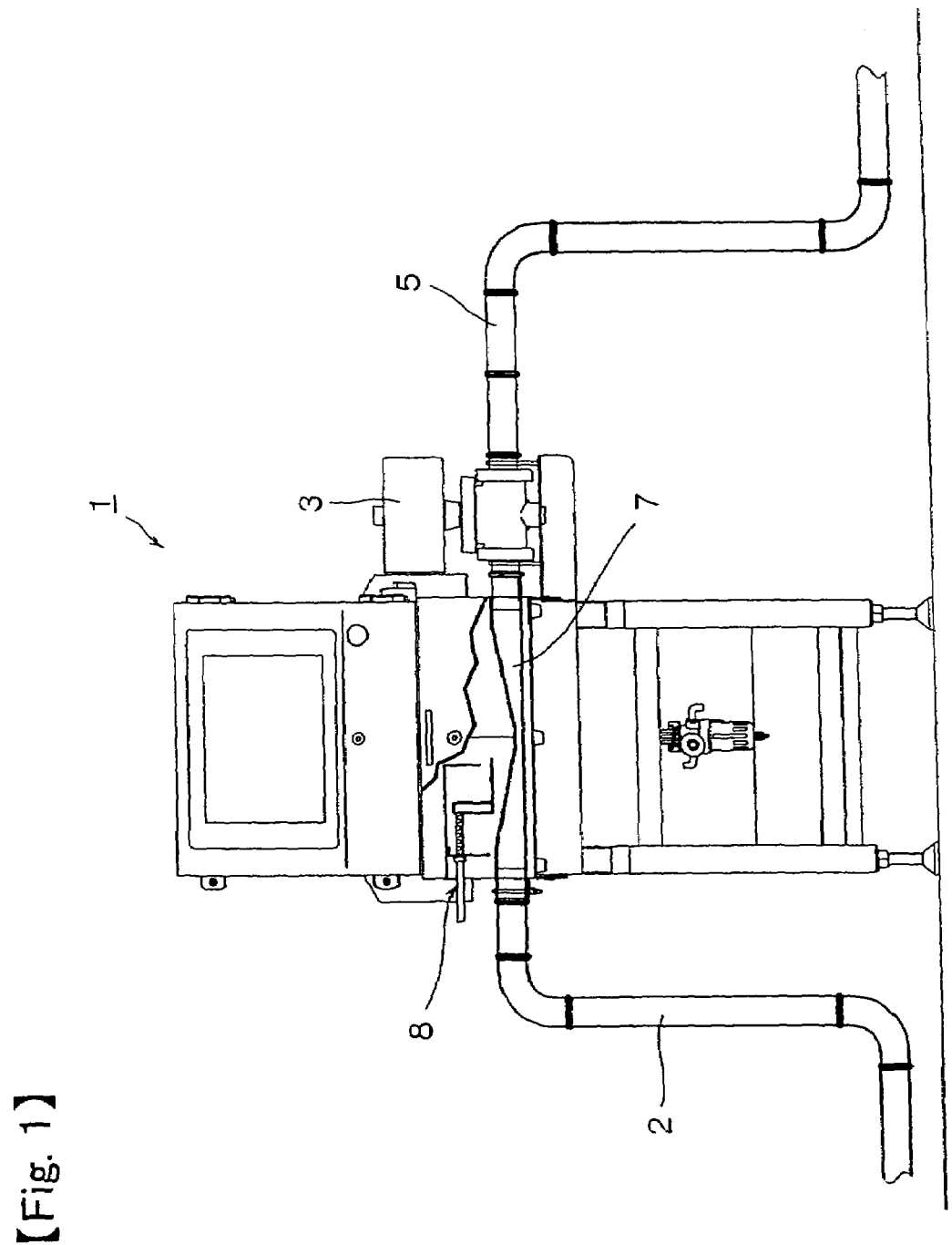
[Fig. 1]

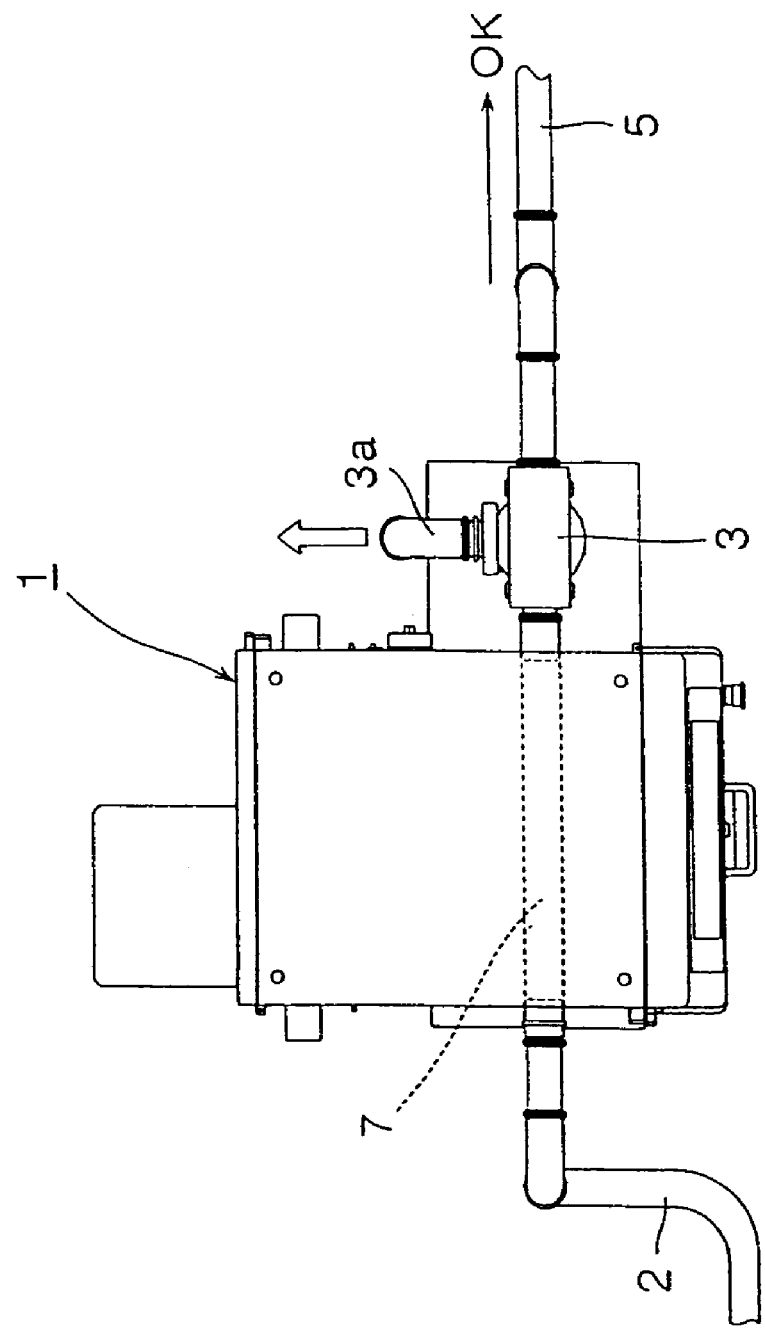
[Fig. 2]

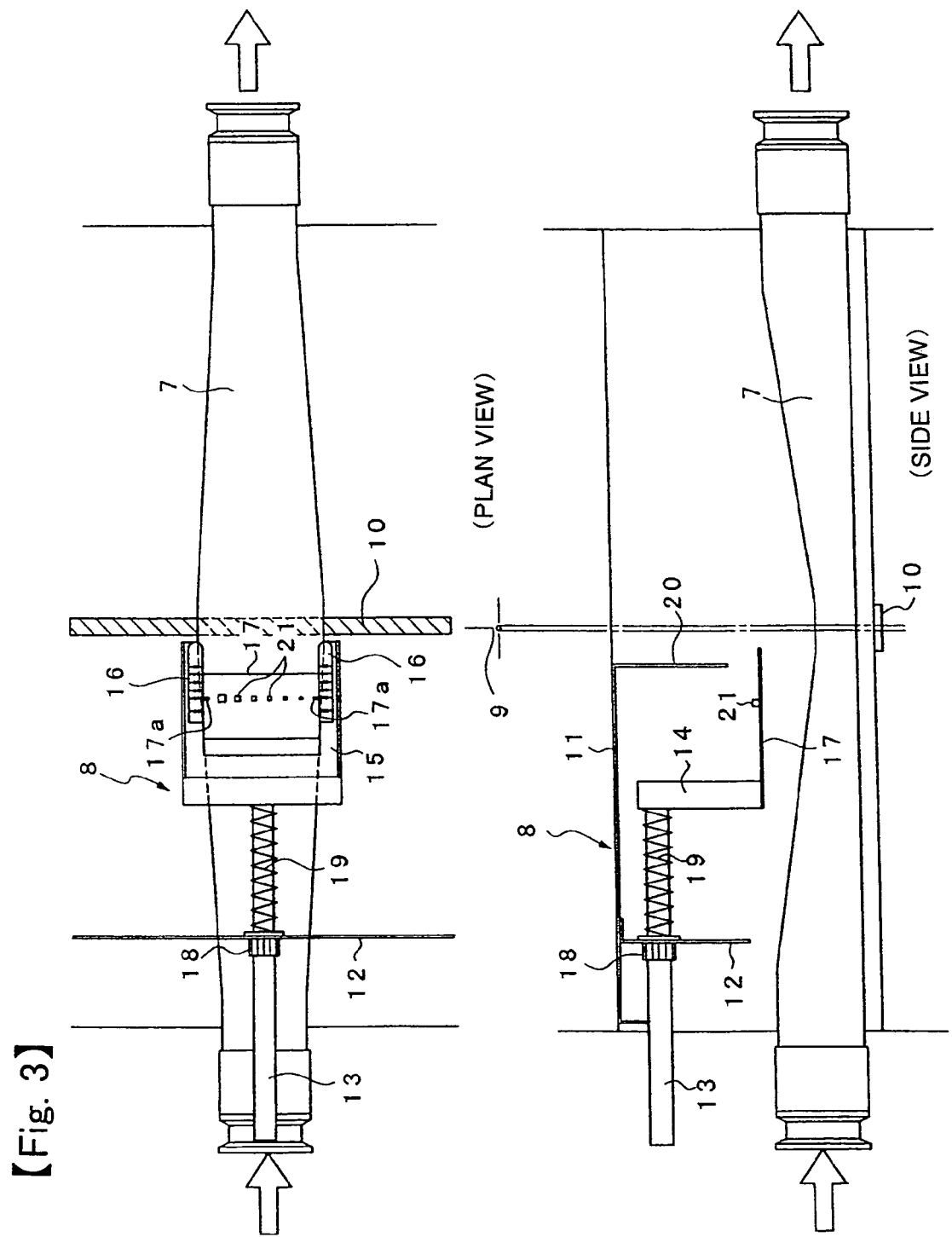
[Fig. 3]

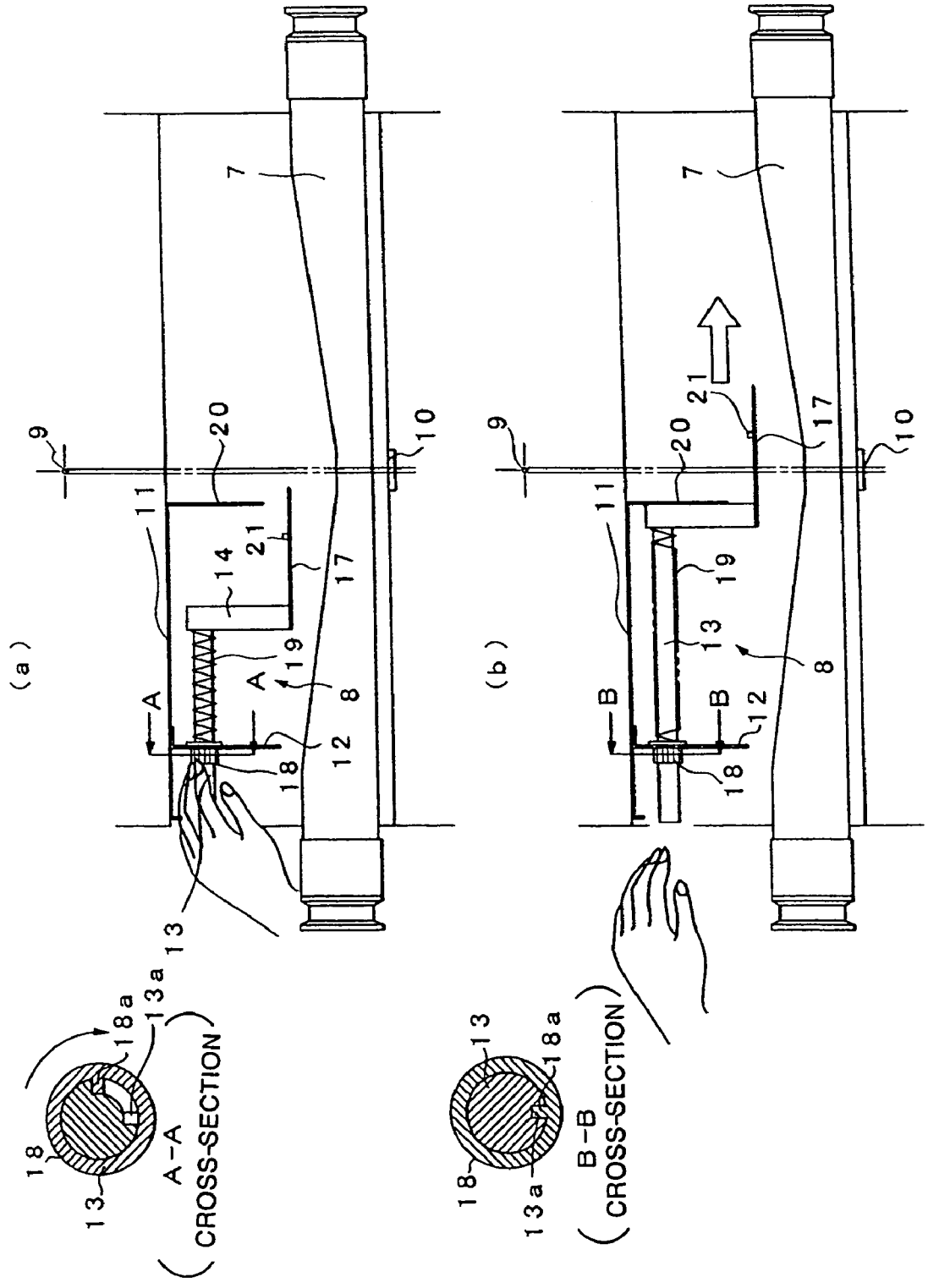
[Fig. 4]

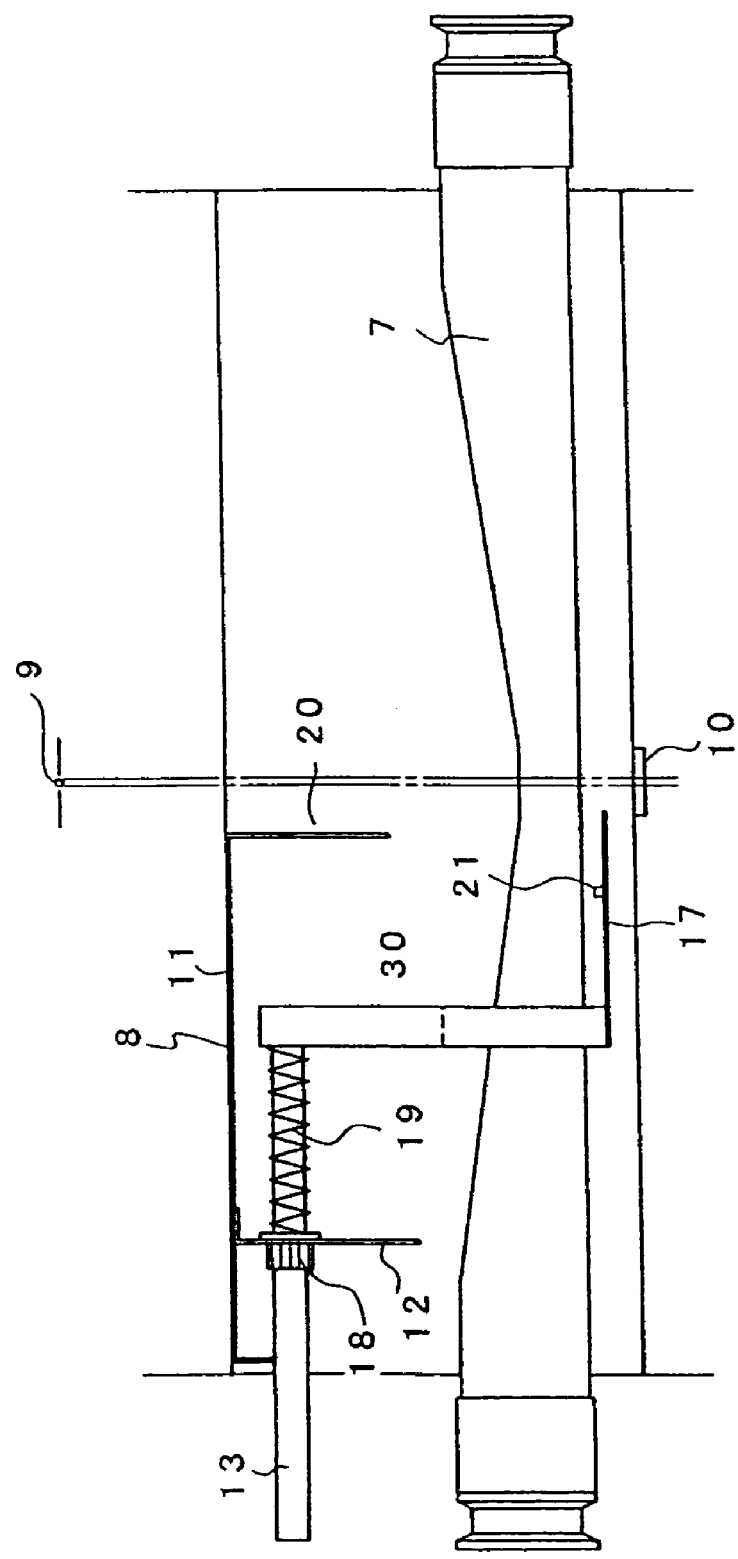
[Fig. 5]

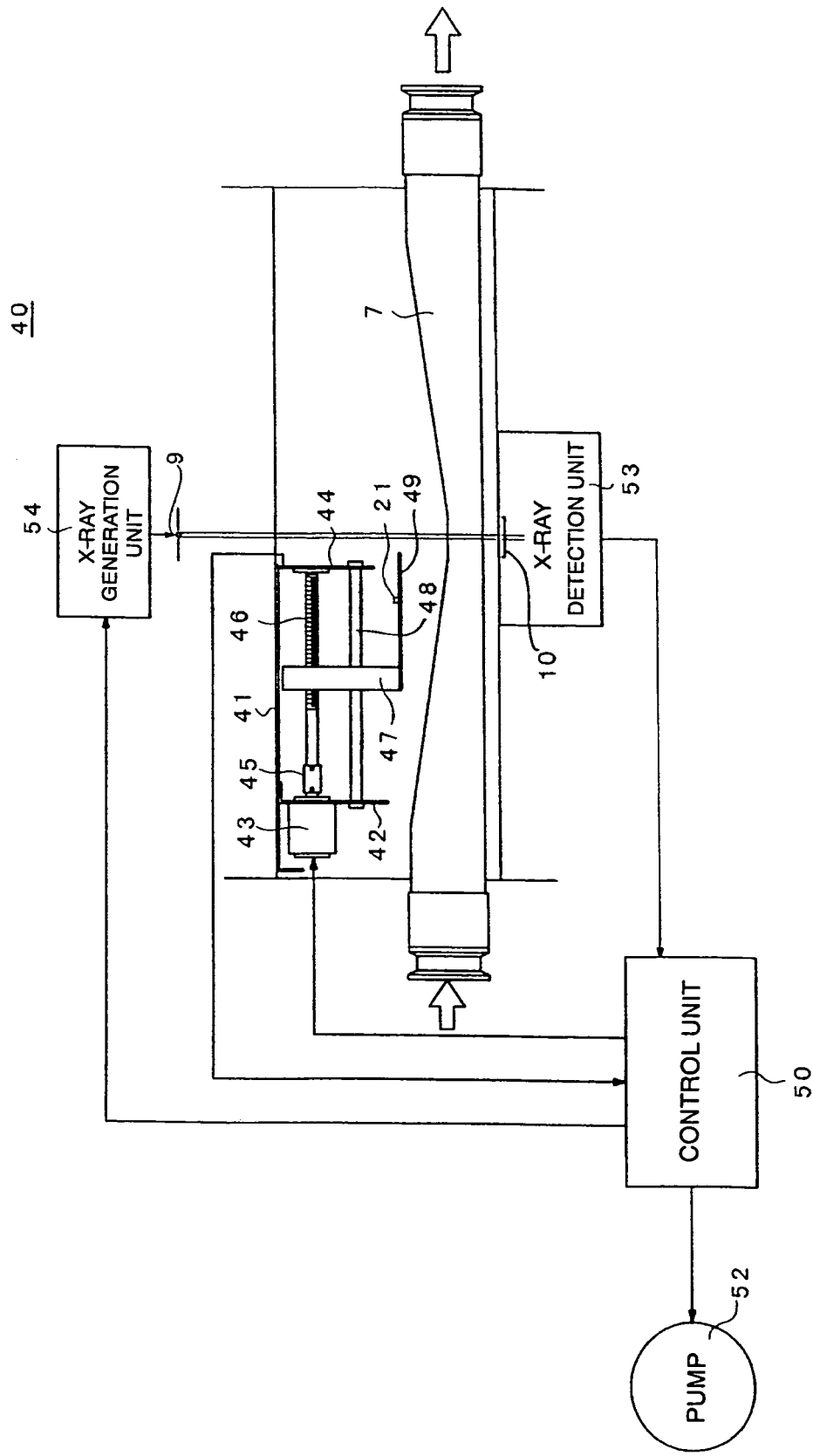

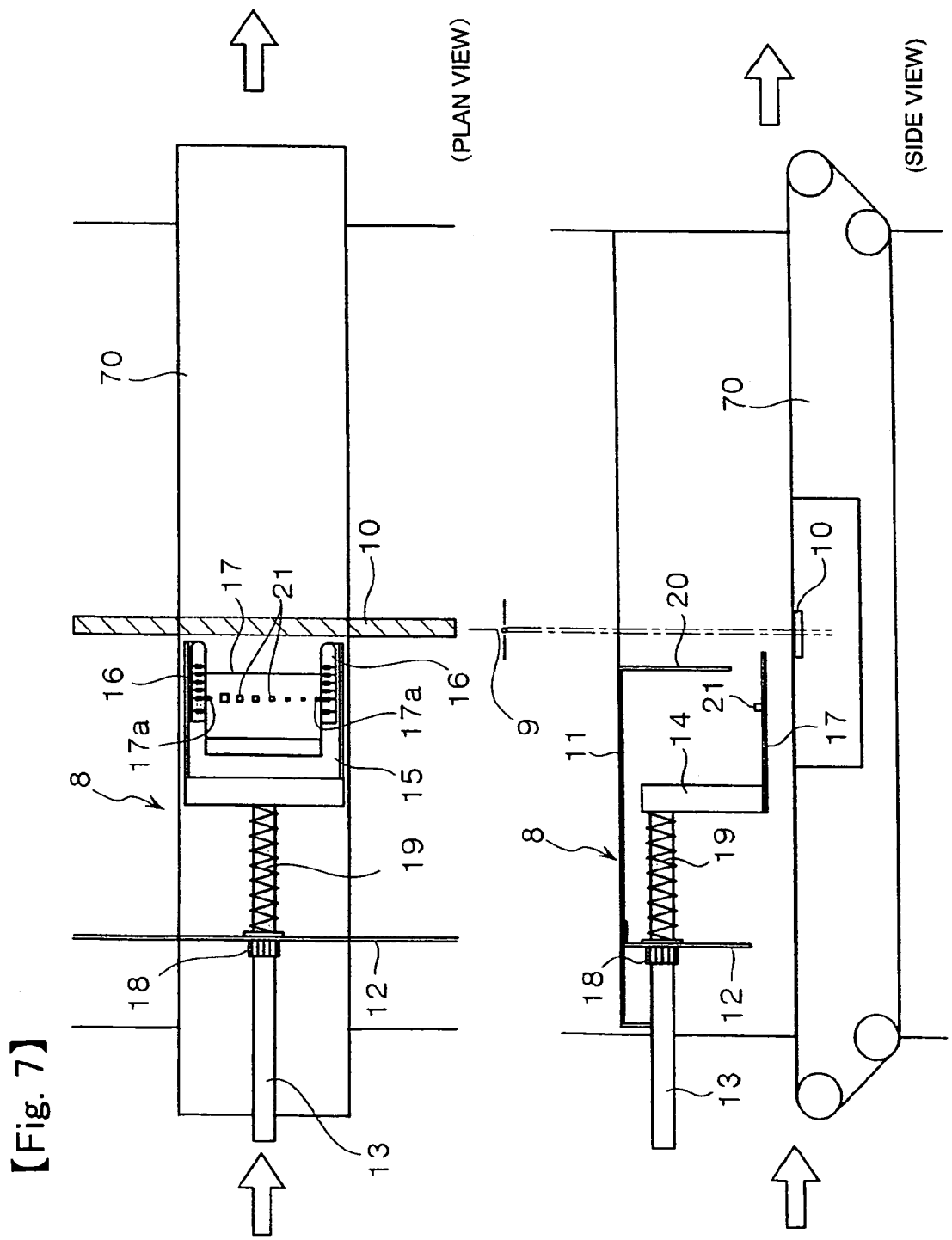
[Fig. 7]

[Fig. 8]
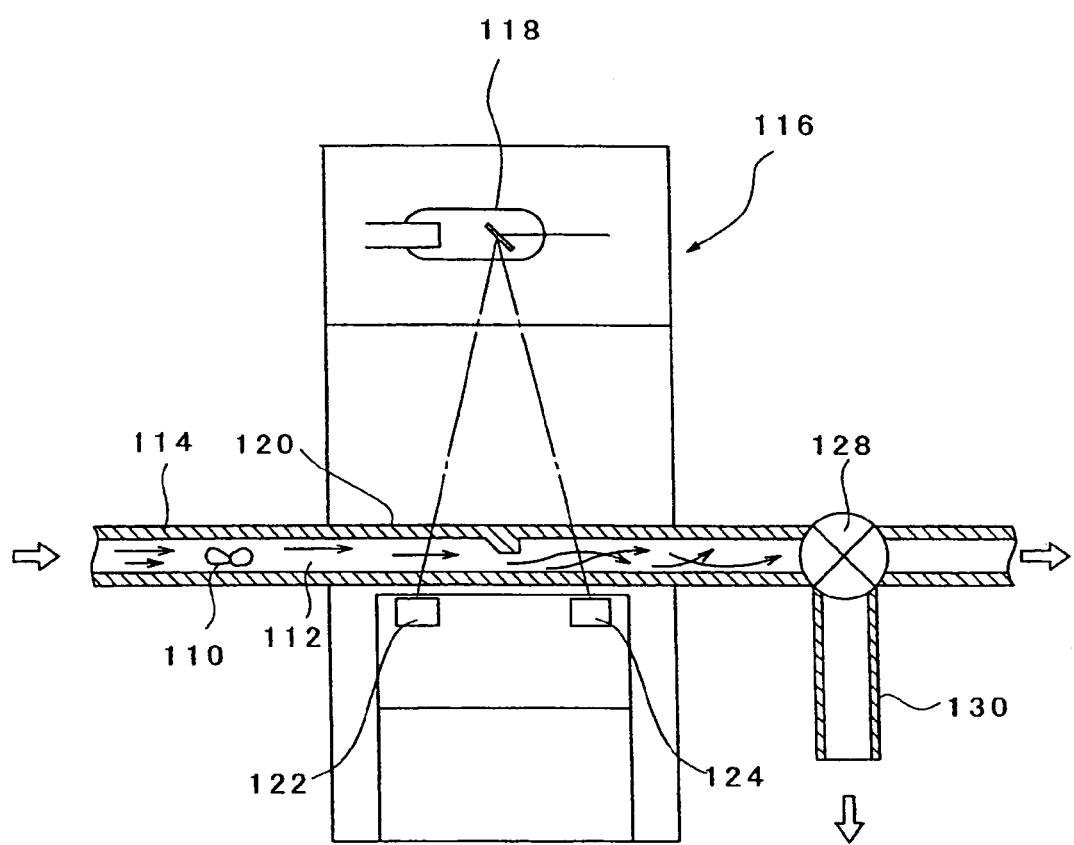

X-RAY DETECTION DEVICE FOR FOREIGN MATTER

TECHNICAL FIELD

The present invention relates to a detection device which irradiates an examination subject article being conveyed with X-rays and detects foreign matter mixed in the examination subject article on the basis of the transmission amount of X-rays that have penetrated the examination subject article. More particularly, it relates to a mechanism which moves a test piece at a speed substantially the same as the moving speed of the examination subject article for the purpose of adjusting the sensitivity of detection by use of X-rays.

BACKGROUND ART

X-ray inspection devices have conventionally been in use to detect foreign matter (such as metal, glass, shells, bones, etc.) mixed in an examination subject article, for example, food. Generally, an X-ray detection device for foreign matter has a configuration in which examination subject articles being conveyed by conveyance means are sequentially examined. For the conveyance means to be used, a type of means suitable for the type of the examination subject articles is selected.

For example, to convey foodstuff such as stripped shellfish like stripped short neck clams, fish paste, retort food materials, and soup with fillings, a pipeline and means for moving an examination subject article in the pipeline, for example, a pump are used. When the examination subject article to be conveyed in the pipeline includes solid materials such as stripped short neck clams or retort food materials, they are fluidly conveyed in the pipeline together with a conveyance fluid (for example, water). When the examination subject article to be conveyed in the pipeline includes fluid materials or solid materials mixed with a fluid such as fish paste or soup with fillings, the examination subject article is fluidly conveyed as it is in the pipeline using no conveyance fluid.

An example of an X-ray detection device for foreign matter using a pipeline as conveyance means as described above is disclosed in Patent Reference 1 (Japanese Patent Laid-Open No. 2591171). The X-ray detection device has, as shown in FIG. 8, an X-ray detection section 116 to which an examination subject article (including a stripped shellfish 110, foreign matter such as shells and metal pieces, and a conveyance fluid 112) is supplied from a supply tank, not shown, through a pipeline 114. In the X-ray detection section 116, the examination subject article is irradiated, at a prescribed timing, with X-rays emitted from an X-ray generation tube 118 through a pipeline 120 communicated to a downstream portion of the pipeline 114. Then, X-rays having penetrated the examination subject article are measured at constant intervals by plural X-ray sensors 122 and plural X-ray sensors 124. The X-ray sensors 122 and the X-ray sensors 124 are respectively arranged in a direction crossing the pipeline 120.

When a foreign matter detection signal is outputted from a signal processing section, not shown, based on the results of measurement by the X-ray sensors 122 and 124, a discharge valve 128 is operated to guide the portion containing foreign matter of the examination subject article into a pipeline 130 for discharge.

The upstream pipeline 114 is made of a stainless steel pipe (SUS pipe) and the downstream pipeline 120 is made of a resin pipe which is X-ray transmissive.

To check and adjust the foreign matter detection sensitivity of the above X-ray detection device for foreign matter, test pieces are used. When checking and adjusting the detection sensitivity, plural kinds of test pieces are prepared according to the kinds and sizes of foreign matter expected to be detected. The test pieces thus prepared are made to flow, together with a fluid, in the pipeline at speed similar to the flow speed used in real detection operation and are irradiated with X-rays under conditions similar to those under which real detection operation is carried out. By doing so, what sizes of test pieces can be detected under the conditions can be determined, so that it becomes possible to adjust and determine, for the size of foreign matter to be detected, the conditions (for example, fluid velocity in the pipeline and the intensity of X-rays) under which detection operation is to be carried out.

As described above, to check the foreign matter detection sensitivity of an X-ray detection device for foreign matter used to detect foreign matter mixed in an examination subject article being fluidly conveyed in a pipeline, it is necessary to carry out checking by actually flowing test pieces in the pipeline. To carry out such checking, the pipeline requires to be provided with an appropriate inlet at its front stage, which complicates the device configuration. Furthermore, since test pieces different from an examination subject article are put in the pipeline every time such checking is carried out, it is necessary to clean inside the pipeline after the checking. This leads to a problem of making operation troublesome.

The present invention solves the above problems. An object of the present invention is to provide an X-ray detection device for foreign matter provided with a mechanism which allows the sensitivity of foreign matter detection by use of X-rays to be checked by using a simple configuration and performing simple operation without requiring test pieces to be mixed in an actual examination subject article.

DISCLOSURE OF THE INVENTION

The X-ray detection device for foreign matter (1, 40) described in claim 1 irradiates an examination subject article being conveyed in a conveyance path (a range or space through which an examination subject article is conveyed) with X-rays at a predetermined detection position and determines, on the basis of the transmission amount of X-rays that have penetrated the examination subject article, whether or not foreign matter is mixed in. The device is characterized in that it includes a test-piece table (17, 49) which, being outside the conveyance path, holds a test piece (21) for checking sensitivity of detecting the mixed-in foreign matter and which is movably installed so that it can pass the detection position along a moving direction of the examination subject article moving in the conveyance path; and means (19, 43) for moving the test-piece table along the moving direction at substantially the same speed as a moving speed of the examination subject article.

The X-ray detection device for foreign matter described in claim 2 is characterized in that, in the X-ray detection device for foreign matter described in claim 1, the conveyance path is provided inside a pipe (7) in which the examination subject article moves, and the test-piece table (17, 49) is configured such that, in a section of a prescribed length of the conveyance path including the detection position, the table can move substantially in parallel with the moving direction of the examination subject article.

The X-ray detection device for foreign matter described in claim 3 is characterized in that; in the X-ray detection device for foreign matter described in claim 1, the conveyance path is provided as a moving range for the examination subject article placed on a conveyor; and the test-piece table (17, 49)

is configured such that, in a section of a prescribed length of the conveyance path including the detection position, the table can move substantially in parallel with the moving direction of the examination subject article.

The X-ray detection device for foreign matter (1) described in claim 4 is characterized in that, in the X-ray detection device for foreign matter described in claim 1, the means for moving is an elastic body (spring 19).

The X-ray detection device for foreign matter (40) described in claim 5 is characterized in that, in the X-ray detection device for foreign matter described in claim 1, the means for moving is a motor (stepping motor 43).

The X-ray detection device for foreign matter (1, 40) described in claim 6 is characterized in that, in the X-ray detection device for foreign matter described in claim 1, the means for moving is an air cylinder.

The X-ray detection device for foreign matter (1, 40) described in claim 7 is characterized in that, in the X-ray detection device for foreign matter described in one of claims 5 and 6, the moving speed of the examination subject article is arbitrarily settable, and the moving speed of the test-piece table (17, 49) is set according to the set moving speed of the examination subject article.

According to the present invention, checking (measuring and adjusting) the sensitivity of detecting foreign matter by use of X-rays does not require the test piece (21) to be put in an examination subject article flowing in a pipeline. Therefore, checking operation can be carried out very easily without requiring to touch the pipeline and the examination subject article flowing in the pipeline.

According to the invention of claim 4, the configuration in which the test piece (21) is moved outside the pipeline at speed equivalent to the speed of the examination subject article flowing in the pipeline is simple, so that the configuration can be easily incorporated in an existing X-ray detection device for foreign matter.

According to the invention of one of claims 5 and 6, checking operation in which the test piece 21 is moved can be carried out automatically.

According to the invention of claim 7, when fluid speed is changed, the detection sensitivity can be checked by moving the test piece 21 at speed automatically adjusted according to the change in fluid speed. This has an effect of making operation simpler and more reliable.

BRIEF DESCRIPTION OF THE DRAWINGS

FIG. 1 is an overall front view of an X-ray detection device for foreign matter according to the present invention in an installed state.

FIG. 2 is an overall plan view of the same.

FIG. 3 shows a plan view and a side view of a principal part of a first embodiment of the X-ray detection device for foreign matter according to the present invention.

FIG. 4 each show a side view of a principal part of the first embodiment in an operating state.

FIG. 5 is a side view of a principal part of a second embodiment of the present invention.

FIG. 6 is a side view of a principal part of a third embodiment of the present invention, schematically illustrating a partial configuration of the embodiment.

FIG. 7 is a side view of a principal part of a fourth embodiment of the present invention.

FIG. 8 is a schematic front view, partly in section, of a conventional X-ray detection device.

BEST MODE FOR CARRYING OUT THE INVENTION

In the following, preferred embodiments of the present invention will be described in detail with reference to the accompanying drawings. FIG. 1 is an overall front view of an X-ray detection device for foreign matter according to the present invention in an installed state. FIG. 2 is an overall plan view of the same. As shown in the figures, the X-ray detection device for foreign matter includes: a case 1; a pipe 2 for feeding an examination subject article which extends on the upstream side of the case 1 and through which an examination subject article is fluidly conveyed using a conveyance pump, not shown; a no-good article discharge pipe 3a connected to one of two ports branching sideward from a three-way valve 3 on the downstream side of the case 1; and a good article discharge pipe 5 connected to the other of the two ports.

The three-way valve 3 can switch the flow path at a prescribed timing depending on the result of examination so as to discharge the fluid portion containing detected foreign matter through the no-good article discharge pipe 3a.

An examination pipe 7 is disposed inside the case 1. One end of the examination pipe 7 is connected to the pipe 2 for feeding an examination subject article. The other end is connected to the inlet port of the three-way valve 3. The examination pipe 7 is made of resin to be X-ray transmissive. The examination pipe 7 of the present embodiment has a deformed upper side which is gently V-shaped as shown in FIG. 1 and also as shown enlarged in FIG. 3 to be described later. This causes the circular cross-section of the examination pipe 7 to gradually change toward a middle portion thereof, becoming slender and approximately rectangular at the middle portion corresponding to an examination position where X-rays penetrate the pipe.

The examination pipe 7 is for conveying an examination subject article, so that the interior of the examination pipe 7 constitutes a conveyance path for an examination subject article.

The examination pipe 7 of the present embodiment is deformed as described above, because the distance through which X-rays emitted in a fan shape penetrate the examination pipe 7 at the examination position is desired to be as constant as possible over the entire cross-sectional width of the examination pipe 7 at the examination position. The present invention is, however, also applicable to a configuration in which a straight pipe having the same circular cross-section as the pipe 2 for feeding an examination subject article is connected to the pipe 2, without the above-described deformation.

An X-ray irradiation unit 9, to be described later, is disposed above the deformed middle portion of the examination pipe 7. An X-ray detection sensor 10 is provided below the middle portion of the examination pipe 7 in a position opposing the X-ray irradiation unit 9.

In the above arrangement, when an examination subject article is determined to be a good article as a result of an examination carried out to detect foreign matter by applying X-rays, it is discharged into the good article discharge pipe 5 via the three-way valve 3 to be subsequently transported to a good article collection area. When an examination subject article being conveyed in the examination pipe 7 is found to contain foreign matter, the three-way valve 3 is switched, by the detection output of the sensor, to the no-good article discharge pipe 3a at appropriate timing determined based on the flow speed of the examination subject article, thereby causing only the portion containing foreign matter of the examination subject article to be discharged into a discharge section. Subsequently, the three-way valve 3 can be switched back to the good article discharge pipe 5.

In the present embodiment, an X-ray sensitivity checking device 8 is disposed above and in the vicinity of the inspection pipe 7 in the case 1. To check, using a test piece, the sensitivity of foreign matter detection by use of X-rays, the X-ray sensitivity checking device 8 can make the test piece pass the position for foreign matter detection by use of X-rays by moving, using a spring force, the test piece at speed corresponding to the speed of the examination subject article flowing in the examination pipe 7 and in the same direction as the flow direction of the examination subject article. The checking device 8 according to a first embodiment of the present invention is shown in FIGS. 3, 4(a), and 4(b). FIG. 3 shows a plan view and a side view of the checking device 8. FIGS. 4(a) and 4(b) each show a side view of the checking device 8 in an operating state.

In these figures, reference numerals 9 and 10 denote the X-ray irradiation unit and the detection sensor, respectively. They are disposed in mutually opposing positions with the former being above and the latter being below the examination pipe 7. The X-ray irradiation unit 9 applies X-rays such that the X-rays spread downward in an approximately triangular shape in a plane perpendicular to the longitudinal direction of the pipe 7. The sensor 10 is a line sensor composed of a large number of detector elements arrayed in a row perpendicular to the longitudinal direction of the pipe 7. As described in the foregoing, the examination pipe 7 of the present embodiment has a V-shaped upper side as shown in FIG. 3. The circular cross-section of the examination pipe 7 gradually changes toward a middle portion thereof, becoming slender and approximately rectangular at the middle portion that corresponds to the position of the sensor 10 and that is penetrated by X-rays. Therefore, the distance through which radially applied X-rays penetrate the examination pipe 7 is nearly constant over the entire cross-sectional width of the middle portion of the examination pipe 7.

The checking device 8 has: a horizontal bracket 11 fixed to the ceiling above an interior space (examination space) which is inside the case 1 and in which the pipe 7 is installed; a rod 13 which can move, through a vertical bracket 12 fixed to the underside of the horizontal bracket 11, in a direction parallel to the pipe 7; a block 14 vertically held at an end of the rod 13; a support plate 15 which is held in a horizontal position with its rear end attached to the lower end of the block 14 and which has an opening in a central part of its front end, the opening being a rectangular concave portion; a pair of scale plates 16 disposed on both sides of the support plate 15; a test-piece table 17 which is slidably inserted in the opening so that it can move in the anteroposterior direction in the opening; a lock nut 18 which is rotatably attached to the vertical bracket 12 and through which the rod 13 extends; a compression coil spring 19 which is fit between the lock nut 18 and the block 14 and over the circumference of the rod 13 and which is used as means for moving (drive source for) the test-piece table 17; and a stopper plate 20 formed by vertically bending an end portion of the horizontal bracket 11.

The test-piece table 17 is made of plate material such as an acrylic resin plate which is highly X-ray transmissive. On the upper surface of the test-piece table 17, two or more of the test pieces 21 of different sizes are fixedly arranged by size in a row to be in parallel with the direction in which the large number of the detector elements making up the sensor 10 are arrayed. On the test-piece table 17, cursors 17a are provided each in a position corresponding to the outermost one on each side of the plural test pieces arranged in a row. The position on the support plate 15 of the test pieces can be adjusted using the scale plates 16 as a guide, that is, by adjusting the positions of the cursors 17 relative to the scale plates 16.

According to the present embodiment, the examination pipe 7 has a deformed middle portion, so that the cross-section of the middle portion is not circular. It is slender and approximately rectangular with its width being larger than the diameter of the circular cross-section of the pipe. In the present embodiment, the entire width of the slender and approximately rectangular cross-section at the examination position of the pipe represents the width of the examination range. Therefore, the test-piece table 17 has a width corresponding to the width of the examination range. The number and spacing of the plural test pieces 21 arranged on the test-piece table 17 have been determined also based on the width of the examination range (see the plan view in FIG. 3). As mentioned in the foregoing, the examination pipe 7 need not necessarily be deformed as in the present embodiment. It may be a straight cylindrical pipe. In cases where such a cylindrical pipe is used, however, the width of the test-piece table 17 and the number and spacing of the plural test pieces 21 are required to be determined based on the inner diameter of the cylindrical pipe. Regardless of whether the examination pipe has a rectangular cross-section or a circular cross-section, the test pieces are required to be arranged on the test-piece table such that they come within the examination range of the examination pipe.

In cases where a straight cylindrical pipe without deformation is used as the examination pipe 7, the test-piece table 17 can be made to move along a path close to the outer circumferential surface of the examination pipe 7, that is, a path closer to the examination subject article than in the present example in which the test-piece table 17 moves, as shown in FIG. 3, along a path considerably away from the concave upper surface of the middle portion of the examination pipe 7. This enables the test pieces 21 to be placed under conditions similar to those under which the examination subject article actually flowing in the examination pipe 7 is placed. Such an arrangement is similar to the arrangement of a second embodiment shown in FIG. 5 to be described later.

The graduations engraved on each of the scale plates 16 are for indicating the moving speed of the test-piece table 17 when checking the sensitivity of foreign matter detection. In actually checking the sensitivity of foreign matter detection, aligning the cursors 17a provided for the test-piece table 17 with the graduation corresponding to the speed of the examination subject article flowing in the pipe 7 causes the test pieces arranged on the test-piece table 17 to pass, when driven by the elastic force of the spring 19, the detection position of the sensor 10 (the X-ray transmission position) at the speed corresponding to the graduation. Thus, the moving speed of the test pieces passing the detection position can be equalized with the speed of the examination subject article, so that the test pieces and the examination subject article can be placed under identical measurement conditions as far as their moving speeds are concerned.

Namely, the speed V of the test-piece table 17 being driven by the spring 19 and passing the detection position is given by the following equation.

$$V = (2E/m - kx^2/m)^{1/2}$$

where k is a spring constant, m is a total mass of the movable part of the checking device 8 including the rod 13, x is the length of deformation of the spring 19 taking place when the test-piece table 17 passes the detection position, and E is the potential energy of the spring 19 in its most deformed state.

Therefore, before the test-piece table 17 starts moving, the deflection of the spring 19 is constant. When the cursors 17a (or the test pieces 21) are positioned forward (rightward as viewed in FIG. 4) relative to the scale plates 16 disposed on the support plate 15, the deflection of the spring 19 occurring when the positions of the cursors 17a pass the detection position becomes relatively large and the speed V of the test pieces passing the detection position becomes relatively low. Conversely, when the cursors 17a (the test pieces 21) are positioned backward (leftward as viewed in FIG. 4) relative to the scale plates 16 disposed on the support plate 15, the deflection of the spring 19 occurring when the positions of the cursors 17a pass the detection position becomes relatively small and the speed V of the test pieces passing the detection position becomes relatively high.

Based on the condition that the deflection of the spring 19 is constant before the test-piece table 17 starts moving, differences resulting from positioning the cursors 17a with respect to the support plate 15 relatively forward and relatively backward as described above are as follows. When the cursors 17a are positioned forward on the support plate 15, they pass the detection position early. Therefore, the deflection of the spring 19 occurring when they pass the detection position is relatively large. In that state, with the deflection of the spring 19 not having been released much, the speed of the test pieces passing the detection position is relatively low. Conversely, when the cursors 17a are positioned backward on the support plate 15, they pass the detection position later than early. Therefore, the deflection of the spring 19 occurring when they pass the detection position is relatively small. In that state, with the deflection of the spring 19 having been released more, the speed of the test pieces passing the detection position is relatively high.

In the present embodiment, as described above, whereas the deflection of the spring 19 is constant before the test-piece table 17 starts moving, the speed of the test pieces 21 passing the examination position can be adjusted, to some extent, as desired by adjusting the positions of the cursors 17a using the scale plates 16 and the cursor 17a as a guide. This is instrumental in making the test pieces 21 move at a speed corresponding to the flow speed of the examination subject article being examined.

FIGS. 3 and 4(a) show the checking device 8 in a state of standing by for operation. In the state, the rear end of the rod 13 is projecting from a side of the case 1 with the spring 19 compressed. The cross-section taken along line A-A as shown in FIG. 4(a) and the cross-section taken along line B-B as shown in FIG. 4(b) show a mechanism for locking the checking device 8 in the standby state. As the cross-sectional drawings show, the checking device 8 is locked in the standby state when a projection 18a projecting on the inner circumference of a rock nut 18 and a groove 13a formed on the outer circumference of the rod 13 are engaged with each other. The groove 13a extending linearly along the axial direction of the rod 13 is bent about 90 degrees in a circumferential direction with the rod 13 in the most receded position. Therefore, while the projection 18a is held in the portion bent by 90 degrees of the groove 13a, the checking device 8 is kept in the standby state with the rod 13 most receded and the spring 19 compressed.

When checking the detection sensitivity, the lock nut 18 locking the rod 13 is manually rotated 90 degrees causing, as shown in FIG. 4(b), the rod 13 to be released and pushed, by the pushing force of the spring 19 used as moving means, toward the position for detecting foreign matter by use of X-rays (position of the sensor 10). As a result, the test pieces 21 pass the range irradiated with X-rays at a prescribed speed and stop upon abutting against the stopper plate 20. Subsequently, the sensitivity of foreign matter detection by use of X-rays is determined based on the size of the smallest test piece 21 detected. When the sensitivity is found to be lower than required, the X-ray output is increased. When the sensitivity is found to be higher than required, the X-ray output is decreased. This process of detection sensitivity checking and X-ray output adjustment is repeated until optimum sensitivity is obtained.

In the present embodiment, the test pieces move along a path closer to the X-ray irradiation unit 9 than is the path along which the examination subject article actually flows in the examination pipe 7. Therefore, a test piece which is as large as real foreign matter mixed in an examination subject article is recognized and detected by the sensor 10 as an object larger than the real foreign matter. Therefore the foreign matter detection sensitivity does not agree with the actual foreign matter detection sensitivity. In the present embodiment, to make up for such a disagreement in sensitivity, the dimension in the conveyance width direction of an object to be detected is correctively calculated as follows, the conveyance width direction being identical with the direction of width of the range for foreign matter detection by use of X-rays and being perpendicular to the conveyance direction.

First, the distance between elements of the sensor 10 is multiplied by the ratio between the distance from the X-ray irradiation unit 9 to an examination subject article (for example, a test piece) and the distance from the X-ray irradiation unit 9 to the sensor 10. The product obtained is made a unit dimension for data on density in the conveyance width direction. Based on the unit dimension, various width dimensions in the conveyance width direction of the examination subject article are calculated.

As for the calculation of various length dimensions in the direction of conveyance of the examination subject article, the conveyance speed is divided by the repetition speed (scan speed), and the quotient obtained is used as a unit dimension for data on density in the conveyance direction. Based on the unit dimension in the conveyance direction, various length dimensions in the conveyance direction of the examination subject article can be calculated.

FIG. 5 shows a second embodiment of the present invention, in which a spring is used as means for moving a test-piece table. In FIG. 5, parts identical with those described for the first embodiment are denoted by the same reference numerals as used in the first embodiment, and their description is omitted in the following. Parts which are different from those described for the first embodiment are denoted by different reference numerals. Such parts are described in the following.

In the present embodiment, the lower end of the block 30 attached to an end of the rod 13 is divided into two parts. The divided end of the block 30 is positioned below the examination pipe 7 with the examination pipe 7 coming between the two parts. The present embodiment is the same as the first embodiment except that the test-piece table 17 on which the plural test pieces 21 are set is fixed, in a horizontal position, to the divided end of the block 30.

In the present embodiment, contrary to the arrangement in the first embodiment, the test pieces 21 are positioned farther from the X-ray irradiation unit 9 than is the examination subject article flowing in the examination pipe 7. In this case, too, the foreign matter detection sensitivity for the examination subject article and that for the test pieces do not agree with each other. Such a disagreement in sensitivity can be eliminated by making corrective calculation as done in the first embodiment.

FIG. 6 shows a third embodiment in which a motor is used as means for moving a guide piece table and in which a process of checking and adjustment is automated.

In FIG. 6, an X-ray detection device for foreign matter 40 has a mechanism including a horizontal bracket 41 fixed to the ceiling above an interior space inside the case; a stepping motor 43 which is fixed to a vertical bracket 42 drooped from a rear portion of the horizontal bracket 41 and which can rotate in forward and reverse directions; a threaded feed rod 46 the front end of which is rotatably supported by a bearing bracket 44 composed of a vertically bent part at the front end of the horizontal bracket 41 and the rear end of which is axially connected to the output shaft of the stepping motor 43 via a joint 45; a mobile block 47 which is a nut member screwed on the feed rod 46; a whirl-stop guide rod 48 the two ends of which are rotatably supported, below the feed rod 46, by the vertical bracket 42 and the bearing bracket 44, respectively, in a state of being inserted through the mobile block 47; and a test-piece table 49 which is fixed, in a horizontal position, to the lower end of the mobile block 47 and on which plural test pieces 21 are arranged. The mechanism including these parts is controlled by a drive signal from a control unit 50.

When checking the sensitivity of foreign matter detection by use of X-rays, the control unit 50 detects the flow speed of the examination subject article flowing in the pipe 7 based on data outputted by a flow speed sensor, not shown. Based on the detected flow speed, the control unit 50 drivingly controls the stepping motor 43 and thereby makes the test-piece table 49 pass the detection position at the same speed as the flow speed of the examination subject article. The control unit 50 also outputs a control signal to an X-ray generating unit 54 in order to drive the X-ray irradiation unit 9 in such a manner as to enable an X-ray detection unit 53 including the sensor 10 to output an appropriate detection signal. As a result, X-rays having penetrated a fluid containing an examination subject article and test pieces cause the X-ray detection unit 53 to output a signal to the control unit 50. In this way, it is possible to determine, based on the sizes of detectable test pieces, the foreign matter detection sensitivity of the X-ray detection device for foreign matter under the current conditions.

In the present embodiment, a process of detection sensitivity checking through adjustment to be made as required can be performed entirely automatically. Even when the conveyance speed is changed, the detection sensitivity can be automatically checked at an automatically adjusted speed.

A configuration may be used in which, in stead of the stepping motor 43, an actuator such as an air cylinder is used to move the test-piece table 48.

In the embodiments described in the foregoing, a conveyance path for the examination subject article is provided inside the examination pipe 7. In a fourth embodiment shown in FIG. 7, the range or space in which the examination subject article placed on a conveyor 70 move constitutes the conveyance path for the examination subject article.

The conveyor 70 makes up conveyance means which includes an endless belt wound around plural rollers including drive rollers and driven rollers and which is horizontally disposed downward of the X-ray irradiation unit 9. The sensor 10 is disposed straight below the X-ray irradiation unit 9 and in contact with the underside of the upper belt span. The test-piece table 17 is disposed above the conveyor 70 at such a height that it does not interfere with the examination subject article placed on the conveyor 70. The test-piece table 17 moves along a path which is in parallel with the conveyance direction of the conveyor 70.

In other respects, the configuration is identical with that of the first embodiment shown in FIG. 3. The configuration is substantially identical with that of the first embodiment also in terms of operation except that the examination subject article is conveyed by the conveyor 70.

In the embodiment shown in FIG. 5, the test-piece table 17 moves along a path below the examination pipe 7. In the fourth embodiment shown in FIG. 7, too, an arrangement may be made such that the test-piece table 17 moves along a path extending between the upper and lower spans of the endless belt with the sensor 10 disposed below the test-piece table 17. A different arrangement may also be made so that the test-piece table 17 moves along a path below the lower span of the endless belt with the sensor 10 disposed below the test-piece table 17.

In all of the foregoing embodiments, the test-piece table 17 is configured such that it can move in substantially the same direction as the moving direction of the examination subject article in a linear section of a prescribed length of either the examination pipe 7 or the path of conveyance by the conveyor 70, the linear section including the examination position (corresponding to the position of the sensor 10). Therefore, with the sensor 10 oriented perpendicularly to the longitudinal direction of the conveyance path and the moving direction of the examination subject article, the moving speed with respect to the sensor 10 is the same between the test pieces 21 on the test piece table 17 regardless of where in the width direction of the conveyance path the test pieces 21 are individually placed. That is, the moving speed is not affected by the position in the width direction. Therefore, the plural test pieces 21 arranged, as shown in FIG. 3, in a row perpendicular to the moving direction of the test-piece table 17 can pass above the sensor 10 at the same time and at the same speed. Thus, they can be tested under the completely same conditions. In a configuration in which the test-piece table cannot move along a path substantially in parallel with the conveyance direction of the examination subject article, the moving speed of each test piece and its position relative to the sensor 10 changes depending on its position on the test-piece table. In such a configuration, the effect as described above cannot be obtained.

The invention claimed is:

1. An X-ray detection device for foreign matter (1, 40) which irradiates an examination subject article being conveyed in a conveyance path with X-rays at a predetermined detection position and which determines, on the basis of the transmission amount of X-rays that have penetrated through the examination subject article, whether or not foreign matter is mixed in, characterized in that the X-ray detection device comprises:
   a test-piece table (17, 49) which, being outside the conveyance path, holds a test piece (21) for checking sensitivity of detecting the mixed-in foreign matter and which is movably installed so that it can pass the detection position along a moving direction of the examination subject article moving in the conveyance path; and
   means (19, 43) for moving the test-piece table along the moving direction at substantially the same speed as a moving speed of the examination subject article.

2. The X-ray detection device for foreign matter according to claim 1, characterized in that:
   the conveyance path is provided inside a pipe (7) in which the examination subject article moves, and
   the testpiece table (17, 49) is configured such that, in a section of a prescribed length of the conveyance path including the detection position, the table can move substantially in parallel with the moving direction of the examination subject article.

3. The X-ray detection device for foreign matter according to claim 1, characterized in that:

the conveyance path is provided as a moving range for the examination subject article placed on a conveyor; and the test-piece table (17, 49) is configured such that, in a section of a prescribed length of the conveyance path including the detection position, the table can move substantially in parallel with the moving direction of the examination subject article.

4. The X-ray detection device for foreign matter (1) according to claim 1, characterized in that the means for moving is an elastic body (19).

5. The X-ray detection device for foreign matter (40) according to claim 1, characterized in that the means for moving is a motor (43).

6. The X-ray detection device for foreign matter (1, 40) according to claim 1, characterized in that the means for moving is an air cylinder.

7. The X-ray detection device for foreign matter (1, 40) according to claim 5, characterized in that:

the moving speed of the examination subject article is arbitrarily settable, and the moving speed of the test-piece table (17, 49) is set according to the set moving speed of the examination subject article.

* * * * *